(12) United States Patent
Wong et al.

(10) Patent No.: US 6,934,584 B1
(45) Date of Patent: Aug. 23, 2005

(54) ENHANCED POWER EFFICIENCY IN IMPLANTABLE CARDIAC STIMULATION DEVICES

(75) Inventors: Louis Wong, Santa Clara, CA (US); Weiqun Yang, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 467 days.

(21) Appl. No.: 10/113,706

(22) Filed: Mar. 27, 2002

(51) Int. Cl.[7] .............................................. A61N 1/365
(52) U.S. Cl. ....................................................... 607/9
(58) Field of Search .............................. 607/9, 12, 28, 607/29, 5; 363/59–61

(56) References Cited

U.S. PATENT DOCUMENTS

| | | | | |
|---|---|---|---|---|
| 3,878,450 A | * | 4/1975 | Greatbatch | ................... 363/60 |
| 4,050,004 A | * | 9/1977 | Greatbatch | ................... 363/59 |
| 5,076,272 A | * | 12/1991 | Ferek-Petric | ................. 607/28 |
| 6,501,986 B1 | * | 12/2002 | Schaldach et al. | ............. 607/5 |

* cited by examiner

*Primary Examiner*—George Manuel
(74) *Attorney, Agent, or Firm*—Steven M. Mitchell

(57) ABSTRACT

Pacing pulse power efficiency is increased in an implantable cardiac stimulation device. The invention includes a cardiac function sensor for sensing cardiac functions. A controller is coupled to the sensor for determining a required cardiac pacing pulse voltage level. A determining means is coupled to the controller for determining a desired battery voltage multiplication factor as a function of the required pacing pulse voltage level. A setting means is coupled to the determining means for setting a battery voltage multiplier to multiply the battery voltage to a level as close as possible to the required pacing pulse voltage level.

19 Claims, 7 Drawing Sheets

ENHANCED POWER EFFICIENCY IN IMPLANTABLE CARDIAC STIMULATION DEVICES

BACKGROUND OF THE INVENTION

1. Field of the Invention

The present invention relates generally to implantable cardiac devices, such as implantable cardiac defibrillators (ICDs). The present invention more particularly relates to increasing power efficiency for pacing pulses in such implantable cardiac devices.

2. Background Art

Implantable cardiac stimulation devices, such as implantable cardiac defibrillators (ICDs), are well known in the art. Such devices may include, for example, implantable cardiac pacemakers and defibrillators either alone or combined in a common enclosure. The devices are generally surgically implanted in a pectoral region of the chest beneath the skin of a patient. The primary components of an ICD include a monitoring and detection mechanism, a capacitor, a battery, a sensing system for detecting an arrhythmia, and a control system for controlling delivery of a capacitive discharge electrical shock in response to a detected arrhythmia. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

ICDs are often employed to monitor a patient's heart to detect arrhythmias, which are irregular heartbeats that feature either very rapid ventricular contractions due to an abnormally rapid heart rate of about 100–240 beats per minute (tachycardia), an excessively slow heartbeat fewer than 50 to 60 beats per minute (bradycardia) or, most commonly, extra or "premature" beats. The most common arrhythmia is atrial fibrillation, which is an abnormal rhythm of the heart (a rapid, chaotic heart rhythm resulting in no effective pumping of blood) that can result in an increased risk of stroke due to the formation of emboli (blood clots) in the heart. More specifically, atrial fibrillation is an abnormality of heart rhythm in which chambers of the heart no longer contract in an organized manner. Heart rate often becomes irregular and may be very fast, producing palpitations. Atrial fibrillation can lead to symptoms of heart failure (shortness of breath, edema, palpitations) and chest pains and, when left untreated, occasionally can lead to stroke.

The heart has a right side and a left side. Each side has a chamber that receives blood returning to the heart (an atrium) and a muscular chamber that is responsible for pumping blood out of the heart (a ventricle). Atria are relatively thin-walled chambers, whereas the ventricles are much more muscular. Blood passes from the atria into the ventricles through two processes. During the resting phase, when the ventricles are not contracting, the tricuspid and mitral valves open. Some of the blood that has accumulated in the atria passively flows through the tricuspid and mitral valves into the right and left ventricles, respectively. The atria then contract, pumping blood out and into the ventricles. Once the ventricles fill with blood, they contract, pumping blood out of the ventricles, into the lungs, and to the body.

Contractions of the different chambers of the heart are normally organized in a specific manner. An electrical impulse travels through the heart's chambers and sets off contractions. The heart's "spark plug" is a small area of specialized heart tissue called the SA node, located in the right atrium. Each time this tissue "fires," an impulse travels first through the right and left atria, signaling these chambers to contract and pump blood into the ventricles, and then travels down into a patch of another specialized heart tissue located between the atria and the ventricles, called the AV node. Electrical-wire-like specialized tissue conducts the impulse down into the ventricles, where it signals the right ventricle to contract and to pump blood out and into the lungs, and signals the left ventricle to contract and pump blood out to the rest of the body. Normal sequence of electrical activation of the chambers of the heart is called normal sinus rhythm.

In atrial fibrillation, normal sinus rhythm does not occur. Instead, multiple "wavelets" of electrical impulses travel randomly through the atria, leading to more or less random activation of different parts of the atria at different times. Because the tissues of the right and left atria are not stimulated to contract in an organized manner, the walls of the atria more or less quiver.

Lack of organized contraction by the atria causes several detrimental things to happen. First, because less blood is pumped into the ventricles, there is less blood circulating throughout the body and blood accumulates in the lungs, causing shortness of breath (dyspnea) and other symptoms of heart failure. Second, because the heart is no longer pumping blood into the ventricles, the blood in the atria (particularly in a small part of the left atrium, the left atrial appendage) becomes relatively stagnant. There is a small but real risk that, over time, the stagnant blood will form a blood clot. If a blood clot forms, it may eventually enter the left ventricle and then get pumped out into the body. If this happens, the clot may travel to the brain, block the flow of blood in a cerebral artery, and cause a stroke.

Third, atrial fibrillation can create chest pain (angina). Multiple disorganized wavelets of electrical activity bombard the AV node with electrical impulses. When a great many electrical impulses are conducted through the AV node down into the ventricles, the ventricles contract very rapidly, producing a very fast heart rate. When the ventricles contract too rapidly, less blood is pumped into the body and blood may "back up" into the lungs. Rapid contraction increases the ventricles' demand for oxygen. The demand may exceed the ability of the coronary arteries to supply the ventricles with oxygen-rich blood, causing angina.

When an ICD detects an arrhythmia (e.g., due to atrial fibrillation), the ICD is often used to deliver an appropriate shock to the patient's heart in an attempt to return the heart to normal sinus rhythm. Sometimes, second, third, and fourth (and possibly more) shocks are required in a critical case to return the heart to normal sinus rhythm.

Current ICDs are battery powered. The battery is implanted in the patient as part of the ICD. The types of batteries used in ICDs vary. Typical ICD batteries supply voltage in the range of 2.8 to 3.2 Volts (V), depending on the battery chemistry. In conventional devices, pacing pulses are regulated by a charge pump circuit that multiplies the battery voltage by an integer multiplication factor (e.g., 1X, 2X, 3X, etc.) to obtain the desired pacing voltage.

In many cases, conventional charge pump systems are not power efficient. For example, with modern advances on the pacing leads and auto-capture system, the required pacing voltages have been significantly reduced (usually to less than 1V). If a 0.7V pacing voltage is needed, it will be directly regulated from the battery. If the battery voltage is 2.8V, the efficiency will be 25%. If the battery voltage is 3.2V, the efficiency will be even lower, on the order of 22%. Similarly, if a 3V pacing voltage is required from a 2.8V battery, the conventional charge pump must use a 2×multiplication factor to increase the battery voltage, resulting in a 54% power efficiency.

Methods and devices are therefore needed to increase power efficiency for the pacing pulses.

SUMMARY OF THE INVENTION

The present invention is directed to an apparatus and method for increasing pacing pulse power efficiency in an implantable cardiac stimulation device. The invention includes a cardiac function sensor for sensing cardiac functions. A controller is coupled to the sensor for determining a required cardiac pacing pulse voltage level. A determining means is coupled to the controller for determining a desired battery voltage multiplication factor as a function of the required pacing pulse voltage level. A setting means is coupled to the determining means for setting a battery voltage multiplier to multiply the battery voltage to a level as close as possible to the required pacing pulse voltage level.

A control signal is generated as a function of the desired battery voltage multiplication factor and the voltage level of the control signal is shifted to approximately the level of the battery voltage. The setting means can be set to multiply the battery voltage by a factor between about 0.33 and about 3.0.

BRIEF DESCRIPTION OF THE FIGURES

Further features and advantages of the present invention may be more readily understood by reference to the following description taken in conjunction with the accompanying drawings. Like numerals or reference designators will be used to refer to like parts or elements throughout.

DETAILED DESCRIPTION OF THE INVENTION

The following description is of the best modes presently contemplated for practicing the invention. This description is not to be taken in a limiting sense but is made merely for the purpose of describing the general principles of the invention. The scope of the invention should be ascertained with reference to the claims.

Exemplary Stimulation Device

Figure 1:
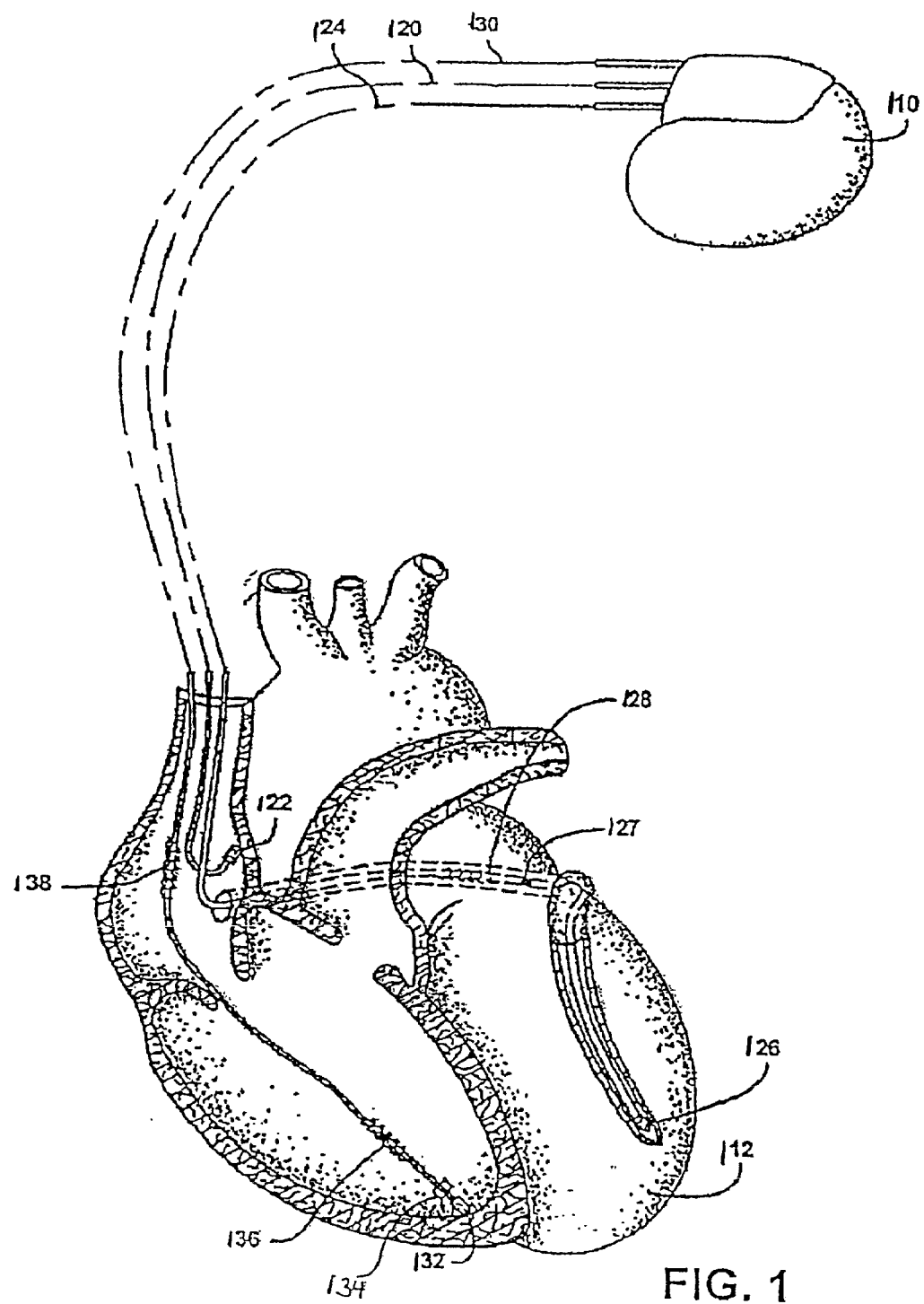
FIG. 1 is a simplified diagram illustrating an implantable stimulation device in electrical communication with at least three leads implanted into a patient's heart for delivering multi-chamber stimulation and shock therapy.

FIG. 1 shows an exemplary implantable cardiac stimulation device 110 (also referred to as a pacing device, a pacing apparatus, or an ICD) in electrical communication with a patient's heart 112 by way of three leads, 120, 124 and 130, suitable for delivering multi-chamber stimulation and shock therapy. To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage.

To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive atrial and ventricular cardiac signals and to deliver left ventricular pacing therapy using at least a left ventricular tip electrode 126, left atrial pacing therapy using at least a left atria ring electrode 127, and shocking therapy using at least a left atrial coil electrode 128.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. As used herein, "pacing," "pacing pulse," and "pacing voltage" means any electrical signal applied to the heart to modify or adjust the heart rate in any way.

Figure 2:
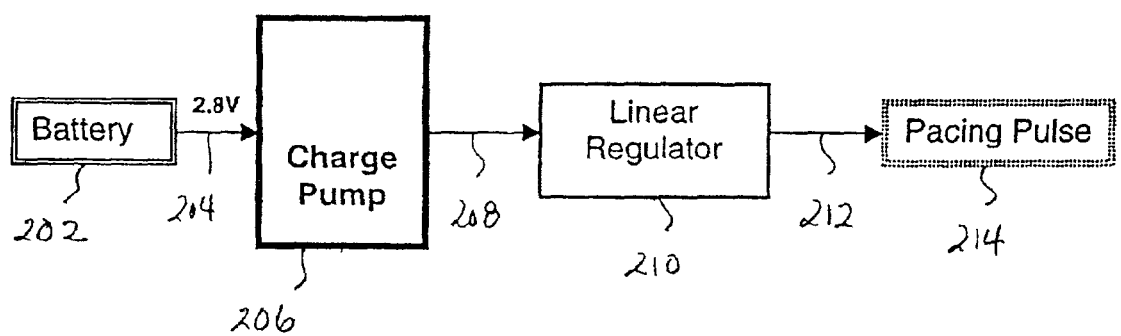
FIG. 2 is a block diagram of the charge pump step-up/step-down circuit of this invention.

To improve power efficiency, the present invention incorporates a charge pump circuit that is capable of stepping up or stepping down the supply voltage by a factor other than an integer multiple of the supply voltage. FIG. 2 is a block diagram of the charge pump circuit elements which comprise the present invention. The circuit elements include a battery 202, a step-up/step-down charge pump circuit 206, and a linear regulator circuit 210. The output of regulator 210 is applied to appropriate pacing pulse supply circuits, generally designated 214. Battery 202 produces a battery supply voltage 204. An exemplary battery produces a supply voltage of about 2.8V. Charge pump 206 steps up or down the battery voltage and produces a charge pump output voltage 208 which is a multiple of battery supply voltage 204. Conventional charge pumps only step up the battery voltage by a factor which is an integer multiple of the battery voltage. Thus the step up factor in a conventional charge pump would be on the order of 2X, 3X, etc., where X is the battery voltage. The present invention, as will be described in more detail below, comprises a charge pump having both step up and step down factors that need not be an integer multiple of the battery voltage. For example, the step up factor may be 1.5, 2.0, 2.5, etc. and the step down factor may be 0.75, 0.66, 0.5, 0.33, 0.25, etc. Regulator circuit 210 stabilizes the output voltage 208 from charge pump 206 to remove fluctuations in battery supply voltage 204 and supplies pacing pulse circuits 214 with a regulated second voltage 212. A typical regulator circuit of the type that can be used in this invention is described in co-pending, commonly assigned U.S. patent application Ser. No. 10/011018, filed Dec. 4, 2001 in the name of Louis Wong, titled REDUCING INTEGRATED CIRCUIT POWER CONSUMPTION IN IMPLANTABLE CARDIAC STIMULATION DEVICES, the disclosure of which is incorporated herein by reference.

Charge pump circuit 206 is a capacitor voltage multiplication/division circuit implemented with multiplier and reservoir capacitors. The connection patterns of the multiplier capacitors determine the multiplication or division factor, or the amount by which battery supply voltage 204 will be increased or decreased to produce a second voltage 208 which is higher or lower than the battery supply voltage 204. The multiplication/division factor is calculated to be as close as possible to the desired pacing voltage to maximize the efficiency of stimulation device 110. Battery supply voltage 204 is increased or decreased according to a multiplication or division factor determined in the stimulation device 110 as described in more detail below. Typical multiplication factors are in the range of 1.5, 2.0, 2.5; typical division factors are in the range of 0.67, 0.5, 0.33, 0.25. One skilled in the art will recognize that the present invention is not limited to the aforementioned multiplication and division factors.

Figure 3:
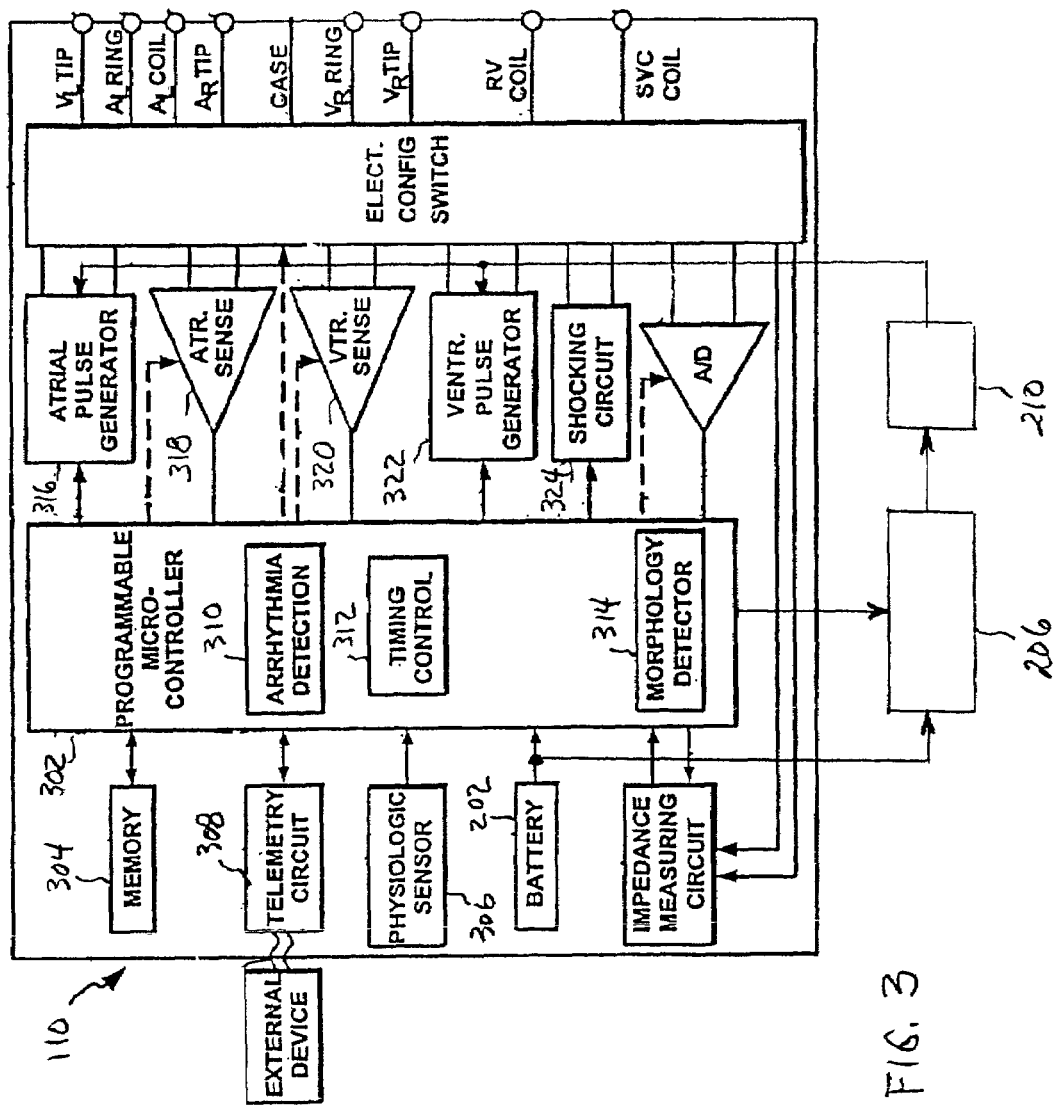
FIG. 3 is an illustration of the elements of the present invention in a functional block diagram of a multi-chamber implantable stimulation device.

FIG. 3 is a simplified block diagram of an exemplary multi-chamber implantable cardiac stimulation device 110 which incorporates the present invention. Stimulation device 110 is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. Additional details of stimulation device 110 are disclosed in co-pending, commonly assigned application Ser. No. 09/861230, filed May 17, 2001 in the name of Mark W. Kroll, titled "METHODS AND DEVICES FOR RAPID DELIVERY OF SECONDARY CARDIAC SHOCKS," the disclosure of which is incorporated herein by reference.

As further shown in FIG. 3, a microcontroller 302 typically includes a microprocessor, or equivalent control circuitry, designed specifically for controlling the delivery of stimulation therapy. The details of the design of microcontroller 302 are not critical to the present invention. The use of microprocessor-based control circuits for performing timing and data analysis functions is well known in the art.

Microcontroller 302 includes timing control circuitry 312 which is used to control pacing parameters. Microcontroller 302 classifies the timing intervals by comparing them to predefined limits and various other characteristics (e.g., physiologic sensors 306, a morphology detector 314, etc.) in order to determine the type of remedial therapy that is needed (e.g., pacing, defibrillation shocks). A sensing system of the present invention, for example, is implemented in the arrhythmia detection software and/or hardware 310 of microcontroller 302. Each sensing circuit, namely atrial sense circuit 318 and ventricular sense circuit 320, in device 110 preferably employs one or more low power, precision amplifiers with programmable gain and/or automatic gain control, bandpass filtering, and a threshold detection circuit, as known in the art, to selectively sense the cardiac signal of interest.

Microcontroller 302 controls atrial and ventricular pulse generators 316 and 322, respectively, via appropriate control signals to trigger or inhibit stimulation pulses and further controls a shocking circuit 324. Microcontroller 302 is also coupled to a memory 304, wherein the programmable operating parameters used by microcontroller 302 are stored and modified, as required, in order to customize the operation of stimulation device 110 to suit the needs of a particular patient. Advantageously, the operating parameters of the implantable device 110 may be non-invasively programmed into memory 304 through a telemetry circuit 308.

Charge pump circuit 206 has one input connected to battery 202 and a second input connected to microcontroller 302. The output of charge pump circuit 206 is applied to regulator 210 as discussed above. The output of regulator 210 is coupled to atrial pulse generator 316 and ventricular pulse generator 322. Using the present invention, the pacing pulses generated by atrial pulse generator 316 and ventricular pulse generator 322 can be controlled to a desired integer or non-integer multiple of the battery voltage to improve the efficiency of the ICD.

Figure 4:
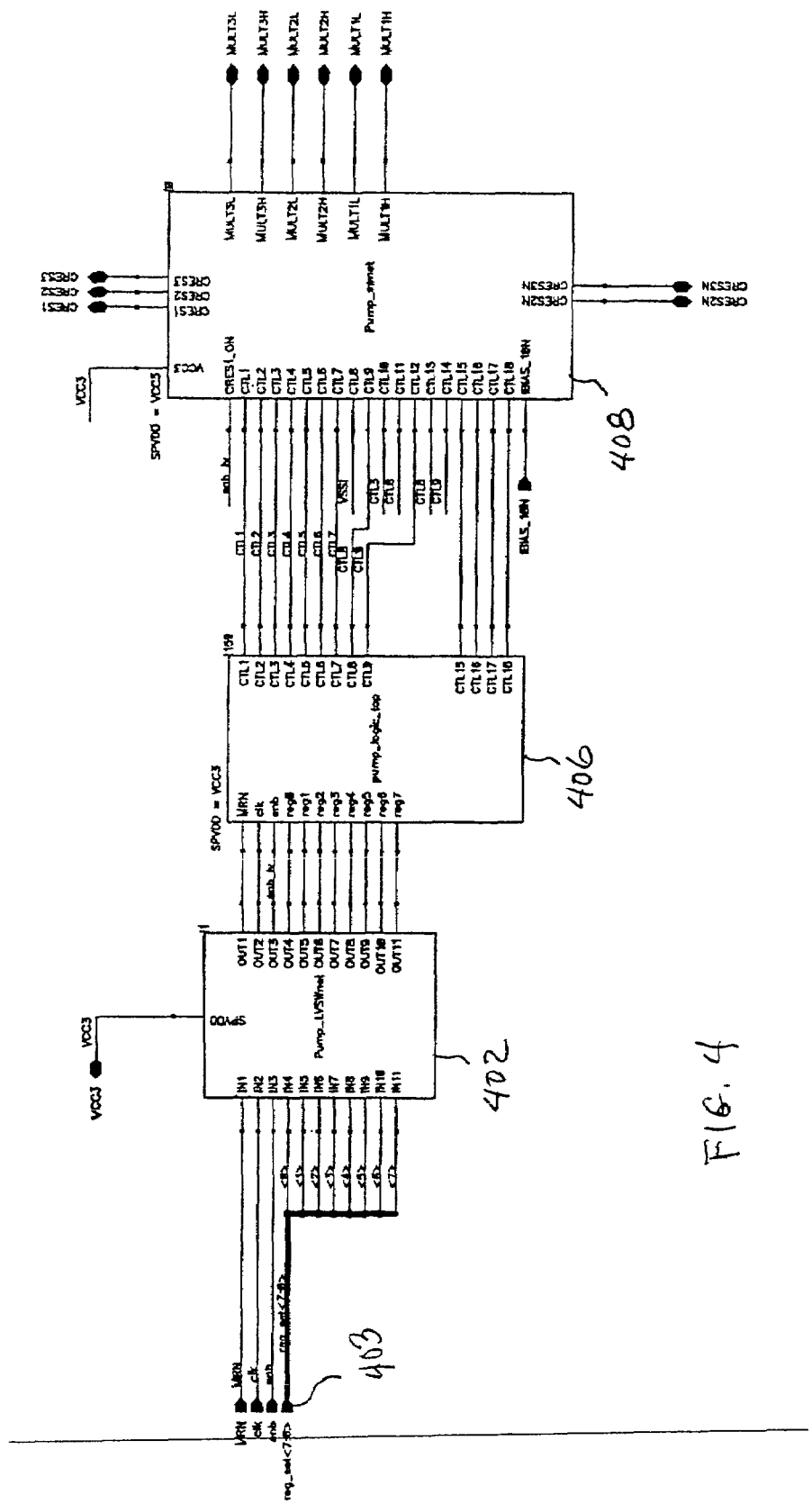
FIG. 4 is a block diagram of the charge pump circuit elements.

FIG. 4 is a block diagram of charge pump circuit 206 that can be used in the present invention. The circuit elements include a logic level shifter 402, a logic block 406 and a voltage multiplier circuit 408. Each of these elements will be described in detail below. Logic level shifter 402 takes its inputs from battery 202, at input VCC3, and from microcontroller 302 at inputs VRN, clk, enb, and reg_set. Logic level shifter 402 shifts the logic level of the microcontroller voltage up to the level of the battery voltage. Pump logic circuit 406 combines clock signals from the microcontroller with register selections (or settings) to provide mode outputs to multiplier circuit 408. Multiplier circuit 408 configures capacitor charging circuits in accordance with control signals from microcontroller 302.

Figure 5:
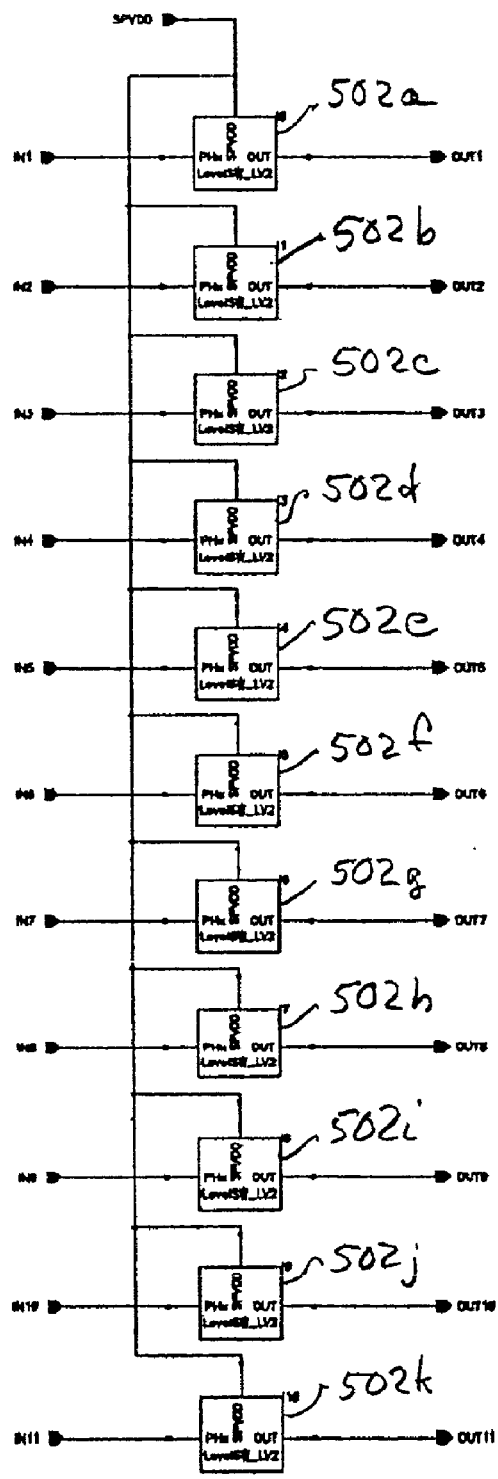
FIG. 5 is a schematic of the logic level shifter of the charge pump.

FIG. 5 shows logic level shift circuit 402. The purpose of the logic level shift circuit is to raise the microcontroller voltage to the level of the battery voltage. Microcontroller 302 controls the step up or step down ratio as a function of inputs obtained from atrial sense circuit 318 and ventricular sense circuit 320. As noted above, the battery voltage is generally in the range of 2.8V. The microcontroller operates at a much lower voltage, for example on the order of 0.9V. It is therefore necessary to step up the microcontroller voltage to the battery voltage so that the pacing pulse can be delivered at the proper voltage level. Logic level shift circuit 402 essentially comprises a buffer or pairs of series-connected inverters 502a–k. The logic pulses generated by microcontroller 302 will be output by level shift circuit 402 with the same timing and swing but at the battery voltage level.

Figure 6:
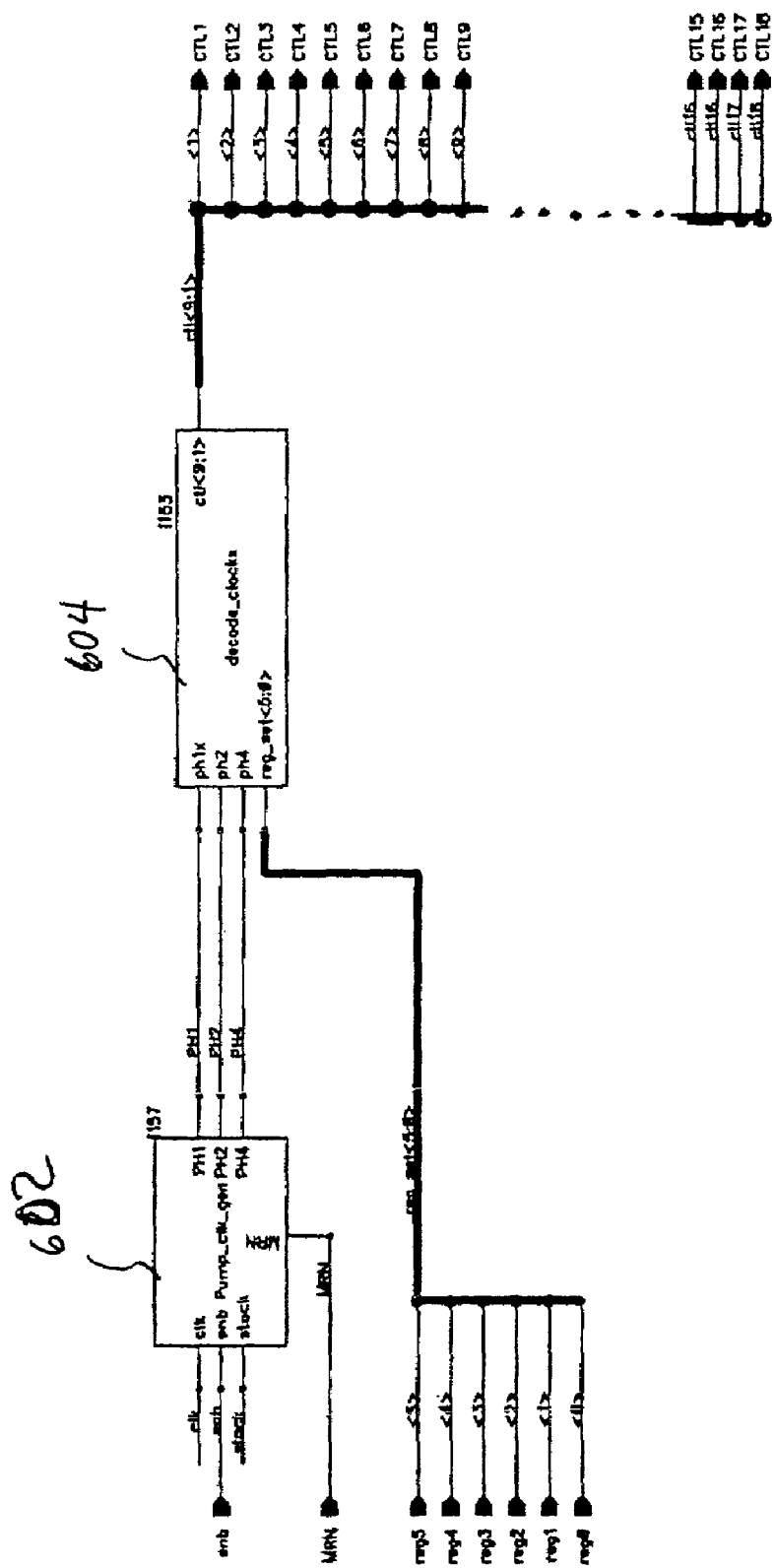
FIG. 6 is a schematic of the charge pump logic circuit.

FIG. 6 shows logic block 406. Logic block 406 sets the voltage multiplication mode based on control signals from microcontroller 302 via logic level shift circuit 402. The multiplication mode settings are provided on outputs CTL1–CTL18 of logic block 406 and are sent to voltage multiplier circuit 408 to configure multiplier circuit 408 for the desired voltage multiplication factor. Logic block 406 comprises a clock generator 602, and a clock decoder or look up table 604. Clock generator 602 generates a non-overlapping clock signal at outputs PH1, PH2 and PH4. Clock decoder 604 combines clock signals PH1, PH2 and PH4 with the register settings from microcontroller 302, as shifted by logic level shift circuit 402, to generate mode control signals CTL1–CTL18.

Figure 7:
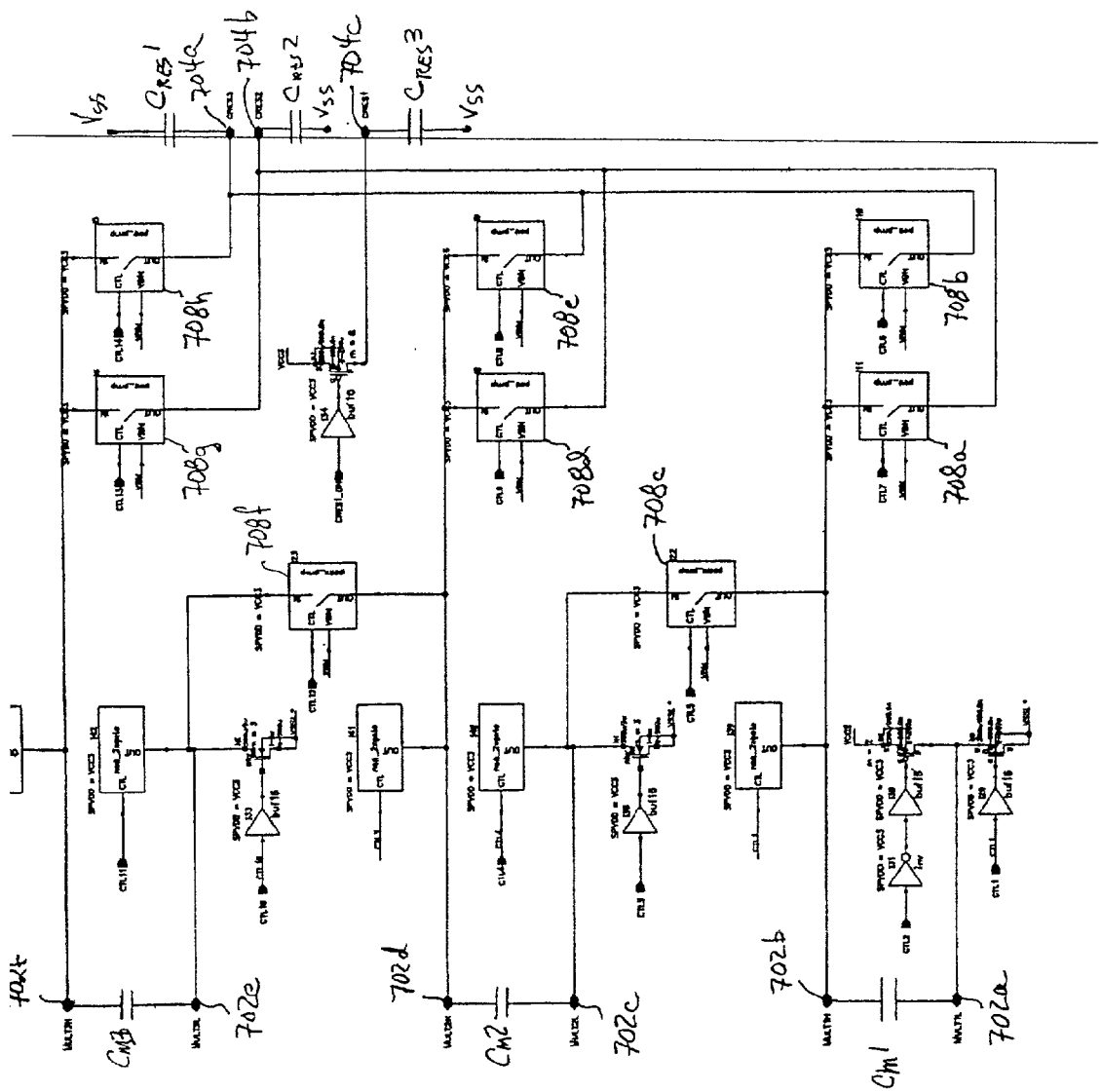
FIG. 7 is a schematic of the step up/step-down switching circuit of the charge pump.

FIG. 7 shows voltage multiplier circuit 408. Multiplier circuit 408 comprises multiplier capacitors CM1, CM2, and CM3 and a plurality of inputs 702a–f. Capacitor CM1 is connected between input leads 702a and 702b. Capacitor CM2 is connected between input leads 702c and 702d. Capacitor CM3 is connected between input leads 702e and 702f. Multiplier circuit 408 further includes a plurality of outputs 704. Outputs 704a, 704b, and 704c each have a reservoir capacitor CRES1, CRES2, and CRES3, respectively coupled between the output and ground. A plurality of switches 708a–708h are coupled between inputs 702 and outputs 704 and serve to connect the multiplier capacitors to the reservoir capacitors in desired configurations as a function of the desired voltage multiplication factor. Typical values for the multiplier capacitors are on the order of 330 nf. Typical values for the reservoir capacitors is on the order of 10 μf. Switches 708 are driven by control signals from outputs CTL1–CTL8 of logic block 406.

By way of example, suppose the pacing pulse is required to be 5.2V. However, the battery voltage is only 2.8V. To supply a pacing pulse that is at or above the required voltage, the battery voltage must be multiplied by a factor of approximately two. This is done as follows. The control signals produced by logic block 406 are digital pulse signals. The signals are generated in two phases: a charging phase and a discharging phase. During the charging phase in the present example, switches 708 are all open. Multiplier capacitors CM1 and CM2 are connected in parallel to battery 202. In this manner, both of capacitors CM1 and CM2 are charged to the battery voltage level of 2.8V. In the discharge phase, switches 708c and 708e are closed by control signals from logic block 406 to thereby connect capacitors CM1 and CM2 in series to output 704a. This connection charges reservoir capacitor CRES1 to twice the battery voltage. Output 704a is coupled to pulse generators 316 and 322 to provide the pacing pulses as needed and as controlled by other portions of microcontroller 302.

By way of another example, suppose the pacing pulse is required to be 0.9V. To supply this pacing voltage, it is necessary to reduce the battery voltage. The closest division to achieve the desired pacing voltage is a division by three. This is accomplished as follows. During the charging phase, control signals from logic block 406 cause switches 708c and 708f to be closed. Multiplier capacitors CM1, CM2, and CM3 are connected in series across battery 202. Each multiplier capacitor is therefore charged to one-third the total battery voltage. During the discharge phase, switches 708b, 708e, and 708h are closed and all the remaining switches are opened. This creates a parallel path to output 704a. Reservoir capacitor CRES1 is thus charged to one-third the battery voltage.

It would be clear to those skilled in the relevant arts from the foregoing description that other multiplication factors can be created by varying the combinational relationships among multiplier capacitors CM1, CM2, and CM3. Microcontroller 302 sets the control signals that are applied to multiplier circuit 408 via logic level shifter 402 and logic block 406.

In operation, atrial and ventricular sensors 318 and 320 sense the functioning of the heart. The readings from sensors 318 and 320 are sent to microcontroller 302. Microcontroller 302 monitors the heart functions and determines when pacing pulses are required to be sent to the heart to stimulate it. Microcontroller 302 also determines the strength of pacing pulses needed at a given time. The voltage of a pacing pulse may range anywhere from about 0.5V to about 5.0V.

After determining the desired timing and strength of the pacing pulses to be administered, microcontroller 302 determines the appropriate multiplication or division factor for the battery voltage. The appropriate factor will be such as to multiply (or divide) the battery voltage to a level as close as possible to the desired pacing pulse voltage level. Microcontroller 302 sends mode control signals to inputs 403 of logic level shifter 402 to increase the voltage level of the microcontroller output signals to the battery voltage level. The voltage level shifted control signals are input to logic block 406 to set the multiplication mode of multiplier circuit 408 and to charge multiplier capacitors CM1, CM2, and CM3 in accordance with the multiplication factor determined by microcontroller 302.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. A method for increasing pulse power efficiency in an implantable cardiac stimulation device, comprising:
    sensing cardiac functions;
    determining a required cardiac pacing pulse voltage level as a function of the sensed cardiac functions;
    determining a battery voltage multiplication factor as a function of the required pulse voltage level; and
    setting the battery voltage multiplier to multiply the battery voltage by a non-integer multiplication factor.

2. The method of claim 1, further comprising:
    generating control signals as a function of the desired battery voltage multiplication factor; and
    shifting the voltage level of said control signals to approximately the level of the battery voltage.

3. The method of claim 2, further comprising setting the battery voltage multiplier to multiply the battery voltage by a factor between about 0.33 and about 3.0.

4. Apparatus for increasing pulse power efficiency in an implantable cardiac stimulation device, comprising:
    a cardiac function sensor for sensing cardiac functions;
    a controller coupled to said sensor wherein the controller determines a required cardiac pacing pulse voltage level as a function of the sensed cardiac functions and wherein the controller determines a battery voltage multiplication factor as a function of the required pacing pulse voltage level; and
    a charge pump adapted to multiply a battery voltage by a non-integer battery voltage multiplication factor.

5. The apparatus of claim 4, further comprising:
    means for generating control signals as a function of the battery voltage multiplication factor; and
    means coupled to said control signal generating means for shifting the voltage level of said control signals to approximately the level of the battery voltage.

6. The apparatus of claim 4 wherein the charge pump is adapted to multiply the battery voltage by a factor between about 0.33 and about 3.0.

7. The apparatus of claim 4 further comprising a regulator circuit coupled to the charge pump that adjusts a charge pump output voltage charge to remove fluctuations in the battery voltage.

8. The apparatus of claim 4 wherein the controller generates control signals to control output of the charge pump as a function of the desired battery voltage multiplication factor.

9. The apparatus of claim 4 wherein the charge pump comprises a logic level shifter coupled to the battery and the controller, the logic level shifter being adapted to shift a logic level of the control signals up to the battery voltage and a mode controller coupled to the microcontroller that sets a voltage multiplication mode of a multiplier circuit in response to the shifted control signals.

10. The apparatus of claim 4 wherein the charge pump comprises a multiplier circuit having a plurality of multiplier capacitors and one or more switches coupled to the plurality of multiplier capacitors, the switches being adapted to couple the plurality of the multiplier capacitors in parallel with a battery to charge each of the multiplier capacitors to the battery voltage.

11. The apparatus of claim 4 wherein the charge pump comprises a multiplier circuit having a plurality of multiplier capacitors and one or more switches coupled to the plurality of multiplier capacitors, the one or more switches being adapted to couple two or more of the plurality of the multiplier capacitors in series with a battery to charge each of the two or more multiplier capacitors coupled in series with the battery to a fraction of the battery voltage.

12. The apparatus of claim 4 wherein the charge pump comprises a multiplier circuit having a plurality of multiplier capacitors coupled between inputs of the multiplier circuit and a plurality of reservoir capacitors coupled between outputs of the multiplier circuit and one or more switches coupled between the multiplier inputs and outputs, the one or more switches being responsive to the controller to couple the plurality of multiplier capacitors to the reservoir capacitors as a function of the battery multiplication factor.

13. An implantable cardiac stimulation device, comprising:
   a battery having a battery voltage;
   a pulse generator coupled to said battery for generating a cardiac pulse;
   a cardiac function sensor for sensing cardiac functions;
   a programmable microcontroller coupled to said sensor for determining a required cardiac pacing pulse voltage level as a function of the sensed cardiac functions;
   determining means coupled to said microcontroller for determining a battery voltage multiplication factor as a function of the required cardiac pacing pulse voltage level; and
   a multiplier circuit coupled to the battery, the multiplier circuit being adapted to multiply the battery voltage by non-integer battery voltage multiplication factor.

14. The apparatus of claim 13, further comprising:
   means for generating control signals as a function of the desired battery voltage multiplication factor; and
   means coupled to said control signal generating means for shifting the voltage level of said control signals to approximately the level of the battery voltage.

15. The apparatus of claim 14, wherein the multiplier circuit is adapted to multiply the battery voltage by a factor between about 0.33 and about 3.0.

16. A method for increasing pulse power efficiency in an implantable cardiac stimulation device, comprising:
   determining a required cardiac pulse voltage level;
   determining a battery voltage multiplication factor as a function of the required pulse voltage level; and
   coupling two or more multiplier capacitors in series with a battery to charge each of the two or more multiplier capacitors to a fraction of the battery voltage and coupling at least one of the two or more multiplier capacitors to an output to generate a multiplier voltage that is a non-integer multiple of the battery voltage.

17. The method of claim 16 further comprising coupling the two or more multiplier capacitors in parallel with a reservoir capacitor coupled between the output to generate a multiplier voltage that is less than the battery voltage.

18. The method of claim 16 further comprising coupling the two or more multiplier capacitors in parallel with a battery to charge each of the multiplier capacitors to the battery voltage.

19. The method of claim 18 further comprising coupling the two or more multiplier capacitors in series with a reservoir capacitor to generate a multiplier voltage that is larger than the battery voltage.

* * * * *